(12) United States Patent
Aggarwal et al.

(10) Patent No.: US 9,021,007 B2
(45) Date of Patent: Apr. 28, 2015

(54) ENABLING INTEROPERABILITY BETWEEN PARTICIPANTS IN A NETWORK

(75) Inventors: Charu C. Aggarwal, Ossining, NY (US); Murray Scott Campbell, Yorktown Heights, NY (US); Yuan-Chi Chang, New York, NY (US); Matthew Leon Hill, Yonkers, NY (US); Chung-Sheng Li, Scarsdale, NY (US); Milind R. Naphade, Fishkill, NY (US); Sriram K. Padmanabhan, San Jose, CA (US); John R. Smith, New Hyde Park, NY (US); Min Wang, Cortlandt Manor, NY (US); Kun-Lung Wu, Yorktown Heights, NY (US); Philip Shilung Yu, Chappaqua, NY (US)

(73) Assignee: International Business Machines Corporation, Armonk, NY (US)

( * ) Notice: Subject to any disclaimer, the term of this patent is extended or adjusted under 35 U.S.C. 154(b) by 1214 days.

(21) Appl. No.: 12/178,980

(22) Filed: Jul. 24, 2008

(65) Prior Publication Data
US 2008/0281626 A1 Nov. 13, 2008

Related U.S. Application Data

(63) Continuation of application No. 10/834,767, filed on Apr. 29, 2004, now abandoned.

(51) Int. Cl.
*G06F 15/16* (2006.01)
*H04L 12/18* (2006.01)
*G06Q 10/06* (2012.01)
(Continued)

(52) U.S. Cl.
CPC ............ *H04L 12/1859* (2013.01); *G06Q 10/06* (2013.01); *G06Q 10/10* (2013.01);
(Continued)

(58) Field of Classification Search
USPC ............................................ 709/201; 705/37
See application file for complete search history.

(56) References Cited

U.S. PATENT DOCUMENTS 6,236,977 B1 * 5/2001 Verba et al. ..................... 705/10
7,149,696 B2 * 12/2006 Shimizu et al. .................. 705/1
(Continued)

FOREIGN PATENT DOCUMENTS

JP 2002300185 A 10/2002

OTHER PUBLICATIONS

Chung-Sheng Li et al., An e-Marketplace Infrastructure for Model-Based Matchmaking between Consumers and Providers of Multimodal Earth Science Data, 2001, IBM T.J. Watson Research Center, pp. 812-815.*
Verna Allee, Reconfiguring the Value Network, Jul. 2000, Journal of Business Strategy, pp. 1-6.*
Berners-Lee et al., "The Semantic Web," http://www.scientificamerican.com, (May 17, 2001).

*Primary Examiner* — Esther B Henderson
(74) *Attorney, Agent, or Firm* — Ryan, Mason & Lewis, LLP

(57) ABSTRACT

Interoperability is enabled between participants in a network by determining values associated with a value metric defined for at least a portion of the network. Information flow is directed between two or more of the participants based at least in part on semantic models corresponding to the participants and on the values associated with the value metric. The semantic models may define interactions between the participants and define at least a portion of information produced or consumed by the participants. The determination of the values and the direction of the information flow may be performed multiple times in order to modify the one or more value metrics. The direction of information flow may allow participants to be deleted from the network, may allow participants to be added to the network, or may allow behavior of the participants to be modified.

32 Claims, 9 Drawing Sheets

(51) Int. Cl.
*G06Q 10/10* (2012.01)
*G06Q 40/04* (2012.01)
*H04L 29/08* (2006.01)
*G06F 19/00* (2011.01)
*H04L 12/58* (2006.01)

(52) U.S. Cl.
CPC ........... *G06Q 40/04* (2013.01); *H04L 67/2823* (2013.01); *H04L 67/125* (2013.01); *G06F 19/3493* (2013.01); *H04L 12/5855* (2013.01)

(56) References Cited

U.S. PATENT DOCUMENTS

| | | | |
|---|---|---|---|
| 2002/0026369 A1* | 2/2002 | Miller et al. | 705/26 |
| 2002/0143560 A1* | 10/2002 | Hanson et al. | 705/1 |
| 2003/0028469 A1* | 2/2003 | Bergman et al. | 705/37 |
| 2004/0210508 A1* | 10/2004 | Bohnenberger | 705/37 |
| 2005/0038688 A1* | 2/2005 | Collins et al. | 705/9 |

* cited by examiner

ADAPTIVE GRID ALIGNING PRODUCERS TO CONSUMERS DYNAMICALLY: STATE 1

ADAPTIVE GRID ALIGNING PRODUCERS TO CONSUMERS DYNAMICALLY:
STATE 2. PRODUCER 2 DROPS OUT

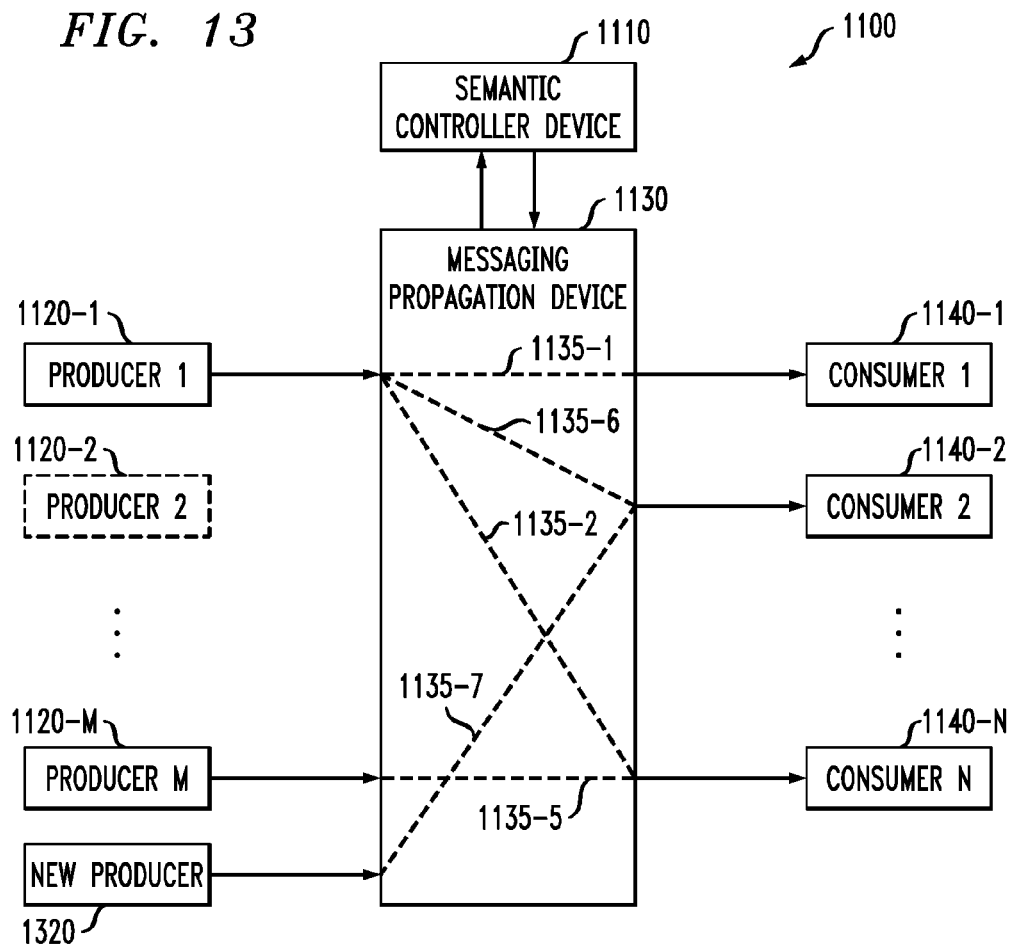
ADAPTIVE GRID ALIGNING PRODUCERS TO CONSUMERS DYNAMICALLY:
STATE 3. A NEW PRODUCER IS ADDED
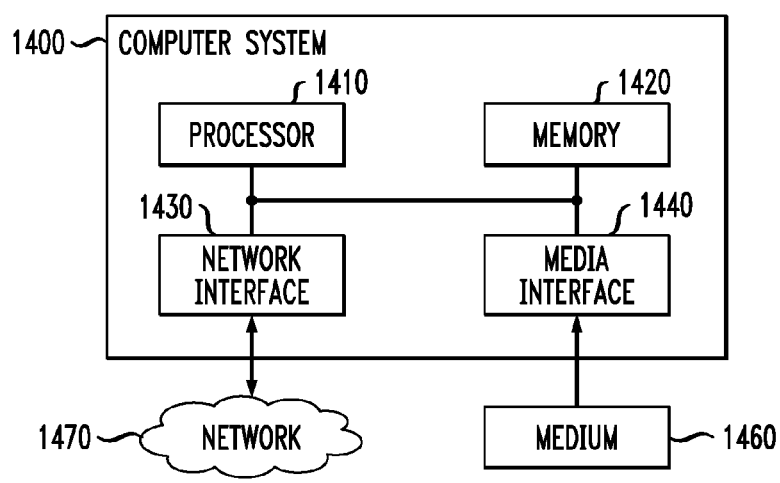

ENABLING INTEROPERABILITY BETWEEN PARTICIPANTS IN A NETWORK

CROSS-REFERENCE TO RELATED APPLICATIONS

This application is a continuation of U.S. patent application Ser. No. 10/834,767, filed Apr. 29, 2004 (now abandoned), incorporated by reference herein.

FIELD OF THE INVENTION

The present invention relates to networking and, more particularly, relates to interactions between participants in a network.

BACKGROUND OF THE INVENTION

By way of example, participants in a network, such as the Internet, can be producers, consumers, and transducers. A producer creates information. As an illustration of a producer, a pharmacy could output to the network the types of Over-The-Counter (OTC) medication purchased during a certain time period. A consumer uses information. Thus, a consumer could be a program that can schedule refills of particular OTC medications when inventory reported by the pharmacy meets a predetermined low level. A transducer transforms the information and creates transformed information. Consequently, a transducer could examine the numbers of remaining bottles of particular OTC medications for certain ailments, such as colds, and determine that one OTC medication is more preferable than another. The transformed information can then be made available to a consumer or another transducer. For instance, a consumer could use this information to schedule more frequent refills of the more preferred OTC medication.

Although networks having participants are valuable, there is a need for providing effective interoperability between the participants in networks.

SUMMARY OF THE INVENTION

Principles of exemplary embodiments of the present invention provide interoperability between participants in a network.

In an aspect of the invention, interoperability is enabled between a plurality of participants in a network by determining one or more values associated with a value metric defined for at least a portion of the network. Additionally, information flow is directed between two or more of the plurality of participants in the network based at least in part on one or more semantic models corresponding to the plurality of participants and on the one or more values associated with the value metric.

The one or more semantic models may define interactions between the plurality of participants and define at least a portion of information produced or consumed by the plurality of participants.

The determination of the one or more values and the direction of the information flow may be performed multiple times in order to modify the one or more value metrics. The direction of information flow may allow participants to be deleted from the network, may allow participants to be added to the network, or may allow behavior of the participants to be modified.

The semantic models may be externalized so that all participants can view the models, and the externalization can involve specifically designed ontologies or federated ontologies or both. Low level metrics may be used when the one or more values of the value metric are determined. The value metric can be simple (e.g., an equation that evaluates to a value) or complex (e.g., a rule).

A more complete understanding of the present invention, as well as further features and advantages of the present invention, will be obtained by reference to the following detailed description and drawings.

BRIEF DESCRIPTION OF THE DRAWINGS

FIG. 13 is a block diagram of the adaptive matchmaking of FIG. 12 at another state in time, when a new producer has been added to the network, in accordance with an exemplary embodiment of the present invention; and FIG. 14 is a block diagram of a computer system suitable for use with embodiments of the present invention.

DETAILED DESCRIPTION OF PREFERRED EMBODIMENTS

Figure 1:
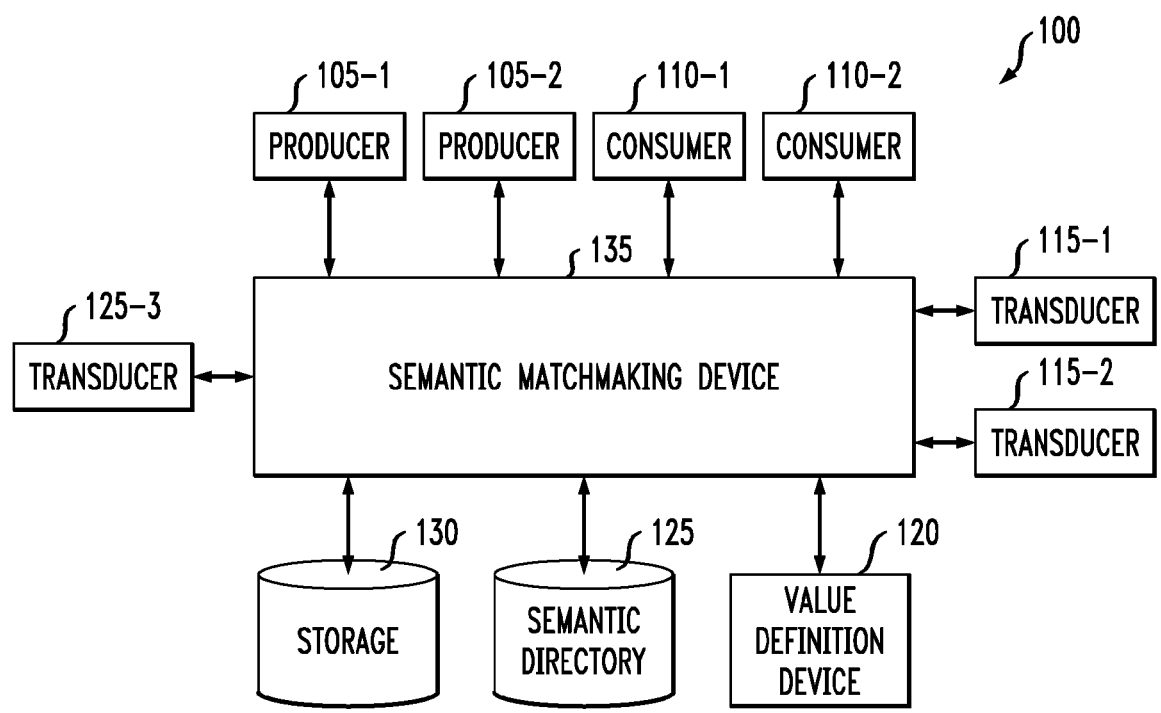
FIG. 1 is a block diagram of a network suitable for enabling interoperability between producers, consumers, and transducers in accordance with an exemplary embodiment of the present invention.

There are certain conventional systems that attempt to provide interoperability. For instance, autonomous management of computing infrastructure is known and provides for self-configuring, self-healing, self-optimizing and self-protecting computing infrastructure. Also known is interoperability amongst low level web services such as the Web Services Description Language (WSDL), as described in Web Services Description Language (WSDL) 1.1 of the World Wide Web Consortium (W3C), W3C Note (March 2001), the disclosure of which is hereby incorporated by reference.

Similarly, there is also a high-level semantic interoperability for web services such as the Semantic Web, as described in J. Handler, T Berners-Lee and E. Miller, "Integrating Applications on the Semantic Web," Journal of the Institute of Electrical Engineers of Japan, Vol 122(10), 676-680 (October 2002), the disclosure of which is hereby incorporated by reference. The main idea of the Semantic Web is to extend the current World Wide Web so that information is given well-defined meaning, thus better enabling computers and people to work in cooperation. The idea is to have data on the Web defined and linked such that the data can be used for more effective discovery, automation, integration and reuse across various applications. The aim is to provide an infrastructure that enables services, sensors, programs and appliances to both consume and produce data on the web.

While the Semantic Web is still more of a goal than an operational infrastructure, several of its components now exist. The components that have emerged include the linking of databases, sharing content among different applications using different eXtensible Markup Language (XML) Document Type Definitions (DTDs) or schemas, and the emerging trends towards Service Oriented Architecture (SOA)-based applications and solutions that incorporate discovery and composition of web services. However, capability beyond that offered by XML-schema is needed to provide mapping capabilities between divergent schemas corresponding to different databases. To this end, a fundamental component of the Semantic Web is the Resource Descriptor Framework. The other related component of the Semantic Web that is related to our invention is the "Semantic Web Services," which brings programs and data together. New protocols and languages are being developed rapidly to standardize the ways in which systems describe what they do. An XML-based protocol called Simple Object Access Protocol (SOAP) has been developed to provide standard means for allowing programs to invoke other programs on the Web. In addition, new web service description and web service languages are emerging. While predefined service definitions may be easier to handle, discovering new services that use different descriptions may not be possible without newly emerging resources such as the web ontology language.

While conventional systems have benefits, there is no existing system that allows interoperability between participants in a network to create a value network. Illustratively, a "value network" is a network that has one or more value metrics associated with the network. The one or more value metrics can be used to improve values associated with the network. The participants of such a value network may adapt from time to time. Additionally, certain components in the value network are adapted to maximize the value, as determined by a value metric, delivered by the network.

In the case of the Semantic Web, for instance, there is no precise notion of "value" as a result of bringing consumers and producers of information together. The "value" created in the Semantic Web is the enabling of services to consume the data. Thus, there is a need for a system that can enable the creation and autonomous maintenance of value networks.

Exemplary embodiments of the present invention can create such a system. One difference between certain embodiments of the present invention and the Semantic Web is that embodiments of the present invention can deliver a network whose value can be modified, such as through optimization, based on matchmaking between the components. In an exemplary embodiment, matchmaking for components directs information flow between components in order to modify a value metric associated with the network and based on semantics provided for the components. For instance, two components will be connected (e.g. through information flow) if semantics indicate the components can be connected and if the network determines that the value metric is (or might be) modified by the connection. The two components are matched when semantics indicate the components can be connected and when the network determines that the value metric is modified by the connection. Once a match is determined, the information flow is directed between the two components. Exemplary embodiments of the present invention allow the interoperability between network participants to be automatic and dynamic.

The following description uses a health monitoring scenario, but embodiments of the present invention are capable of enabling interoperability for value networks for other reasons and are not constrained by the particular application or by the kind of value metric used when enabling interoperability.

FIG. 1 shows a block diagram of a value network 100. Value network 100 can also be considered to be an exemplary framework to enable interoperability of participants in a network. Illustratively, value network 100 can be implemented in a health monitoring scenario by, for example, the Center for Disease Control (CDC), a local health organization, a producer of medications, or a conglomerate of producers of medications, pharmacies, and health organizations. Value network 100 can be implemented by any organization or group of organizations wishing to define a value metric for a network and to modify the value metric.

Participants are specific types of components that can be used to construct a value network, such as value network 100. Value network 100 includes the participants of producers 105-1 and 105-2, the consumers 110-1 and 110-2, and the transducers 115-1 through 115-3. A semantic matchmaking device 135 is coupled to the producers 105-1 and 105-2, the consumers 110-1 and 110-2, and the transducers 115-1 through 115-3, to a value definition device 120, to storage 130, and to a semantic directory 125.

In an exemplary embodiment, the semantic matchmaking device 135 dynamically aligns various network components and allocates resources to optimize a value metric, as defined by the value definition device 120, for which the value network 100 is assembled. Typically, all components of the value network 100 have inputs and outputs associated with them. However, some components, in particular participants, are designed to provide specific inputs to other components while some participants assimilate information from other components to make inferences, detect events and patterns and help predict, forecast or detect specific behavioral properties of the measurements.

In an illustrative embodiment, a purpose of constructing network 100 is to modify, and if possible optimize, a value metric for which the value network is constructed. In the example of FIG. 1, a value definition device 120 is used to define a value metric, which can be user-defined or system-defined. For example, in the domain of health monitoring, the value metric for the network may be the number of days needed to determine when to raise an alarm about a possible outbreak of a health-related epidemic. Therefore, if an alarm for a possible outbreak of a particular health-related epidemic is 10 days, then a decrease in the value metric from 10 days to 9 days is an improvement in the value metric. If the value metric is being optimized, then semantic matchmaking device 135 will perform operations to reduce the number of days needed to raise the alarm. In the case of a business unit, the value metric for the network 100 may be the total sales or total profit based on sales in a particular market or zone. In the domain of human resource management, the value metric may be the employee retention statistic of a particular company.

Typically, a first step in constructing a value network 100 is to identify and externalize a value metric. Externalize means that assumptions (e.g., the value metric) are published so that participants in the network 100 know what the assumptions are. The value metric could be a value such as 100. Alternatively, the value metric could be a rule, such as "minimize the number of days needed to determine when to raise an alarm about a possible outbreak of a health-related epidemic" or "maximize total sales." The value definition device 120 allows a complex metric to be used.

It should be noted that modification of the value metric may not result in optimization of the value metric, although optimization can be a worthwhile technique. Optimization is an optional modification of the value metric. Optimization means that the semantic matchmaking device 135 performs operations to minimize or maximize the value metric. In the case of when the value metric corresponds to one or more values, the semantic matchmaking device 135 optimizes the value metric by maximizing or minimizing the values associated with the value metric. If the value metric is a rule, there are techniques known to those skilled in the art that can be used to determine whether a rule is optimized or not optimized. If the rule is boolean (i.e., evaluates to true or false), optimization can be performed until the rule is true or, if possible, as close to true as can be performed. Furthermore, there could be a case where optimization includes keeping the value metric stable or within a certain range.

It should also be noted that the semantic matchmaking device 135 can also use additional metrics when modifying a value metric defined by the value definition device 120. For example, the consumers 110, for instance, can output metrics that are then used by the semantic matchmaking device 135 when the semantic matchmaking device 135 performs operations to modify the value metric.

Figure 2:
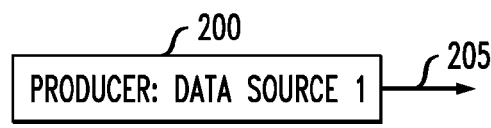
FIG. 2 is an exemplary block diagram of a producer in accordance with an exemplary embodiment of the present invention.

Components of the value network 100 include producers 105-1 and 105-2, which are responsible for producing numerical and qualitative measurements of the phenomena observed by these producers 105. Examples of producers 105 include data sources such as those sources providing sales data. An exemplary producer is shown in FIG. 2. A consumer 110 in a value network accepts as input various information obtained by other components of the network and analyzes the information to detect patterns. Examples of consumers 110 include information analyzers for purposes such as measuring anomalies. A consumer is shown in FIG. 4. A transducer 115 in a value network 100 assimilates information of one kind and generates information of another kind. Examples of transducers 115 include signal processing devices that accept inputs from producers and convert the input into processed information that can be ingested by other transducers or consumers. An exemplary transducer is shown in FIG. 3.

An exemplary producer 200 is shown in FIG. 2. Exemplary producer 200 is a data source that creates an information channel 205. In information channel 205 can be any device or technique suitable for communicating information to another device.

Figure 3:
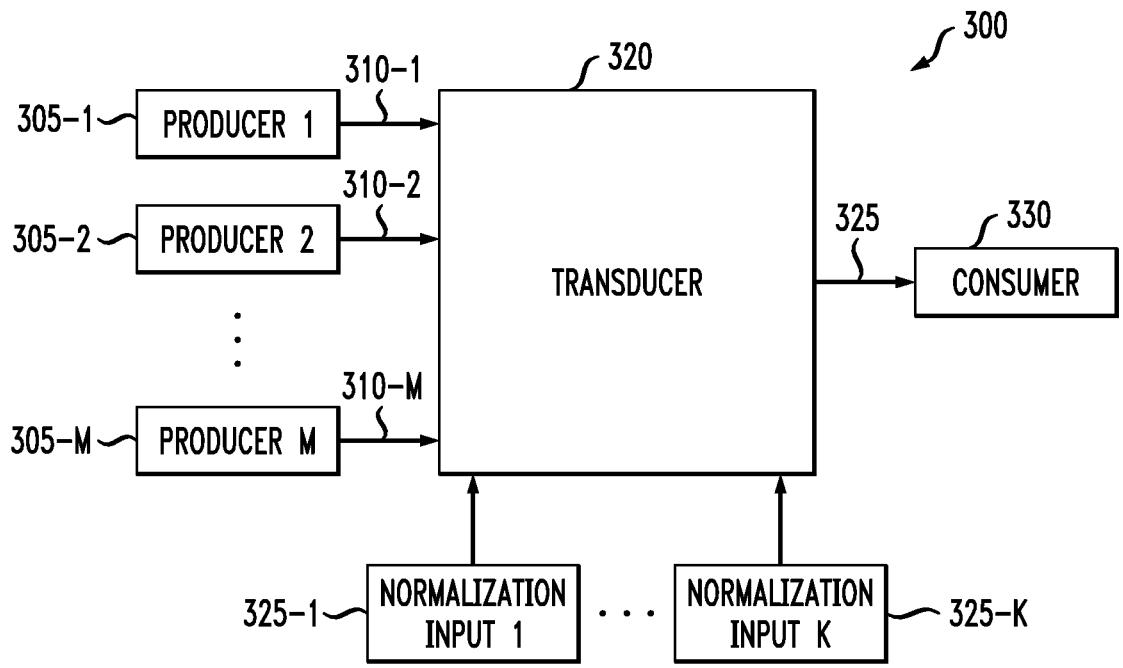
FIG. 3 is an exemplary block diagram illustrating how a transducer might be used as an information source, in accordance with an exemplary embodiment of the present invention.
Figure 4:
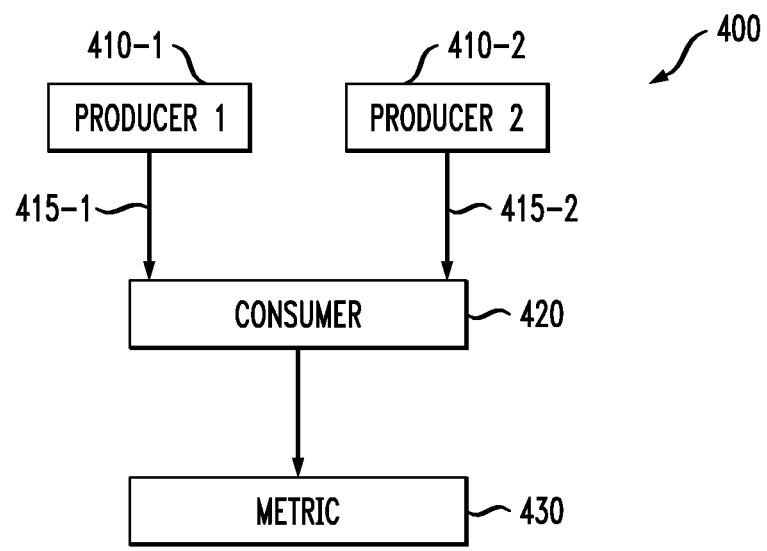
FIG. 4 is an exemplary block diagram illustrating a consumer and possible interactions thereof, in accordance with an exemplary embodiment of the present invention.

FIG. 3 shows an exemplary network portion 300 having a transducer 320 that is coupled to M producers 305-1 through 305-M, to K normalization inputs 325-1 through 325-K and to a consumer 330. A purpose of transduction is to translate the information from one set of observed phenomena to another. Information can be data, knowledge, or any other item that can be transduced. Each producer 305 produces an associated information channel 310. Transducer output 325 is meant to be consumed by other components of the network, such as consumer 330. An example of a transducer 320 in the health monitoring scenario is a network component that accepts as input the total collection of tolls at a particular point on a bridge and converts the total collection into the number of automobiles having crossed the bridge using other information, such as toll charts and camera feeds.

Additionally, a transducer 320 can use normalization inputs 325 to normalize the information on information channels 310. For example, if the population that commutes daily out of a city is known, one could use this information to help normalize relative loads at different outgoing points of congestion. Thus, if there are 1,000 commuters commuting out of the city and 250 commuters pass over one toll bridge, then 25 percent of the commuters pass through this point of congestion. Similarly, if it takes 30 minutes for 250 commuters to pass over a first toll bridge, but takes an hour for 200 commuters to pass over a second bridge, then the transducer 320 could use normalization inputs 325 (e.g., including time during which commuter data was taken) to determine a "commuter rate," which could be used to indicate that the commuter rate for the second toll bridge is lower than the commuter rate for the first toll bridge, even though the number of commuters passing over the second toll bridge is smaller than the number of commuters passing over the first bridge. The consumer 330 could then use this information.

It should be noted that FIG. 3 may also be considered to be a method. The producers 305 perform the step of producing output information, the normalization inputs 325 perform the step of producing normalization information and the transducer 320 transduces and normalizes the output information by using the output information and the normalization information or just transduces the output information.

A network portion 400 is shown in FIG. 4. Network portion 400 contains a consumer 420 that is interacting with two producers 410-1 and 410-2, each producing an information channel 415, and a value metric 430. In this example, producers 410 are shown, but one or both of the producers could be replaced by transducers. In a health monitoring scenario, consumers 420 are typically analyzers of anomalies or patterns of deviation, such as devices that analyze sudden variations in temperature, and the metric 430 determined by the consumer 420 could therefore be related to the temperature. In an exemplary embodiment, consumers 420 in value networks consume processed or raw information from other components to generate derived information pertaining to expertise of the consumer 420. For example, a consumer 420 can be designed to be an expert predictor of hurricanes based on inputs like pressure, wind speeds and relative humidity, and the metric 430 could then be whether or not a hurricane is possible. Consumers 420 can therefore be expert analysis tools.

In the example of FIG. 4, the metric 430 is one of several metrics (not shown in FIG. 4) that are used to help optimize the value metric. For example, the value metric could be the dollar amount of losses incurred through natural disasters in any fiscal year. In the hurricane scenario above, predicting the spatial and temporal location of a hurricane (as indicate by metric 430) can be helpful in minimizing the value metric.

It should be noted that FIG. 4 can also be considered to be a method. For instance, the consumer 420 can perform the step of analyzing information from producers 410 to produce a metric 430.

Figure 5:
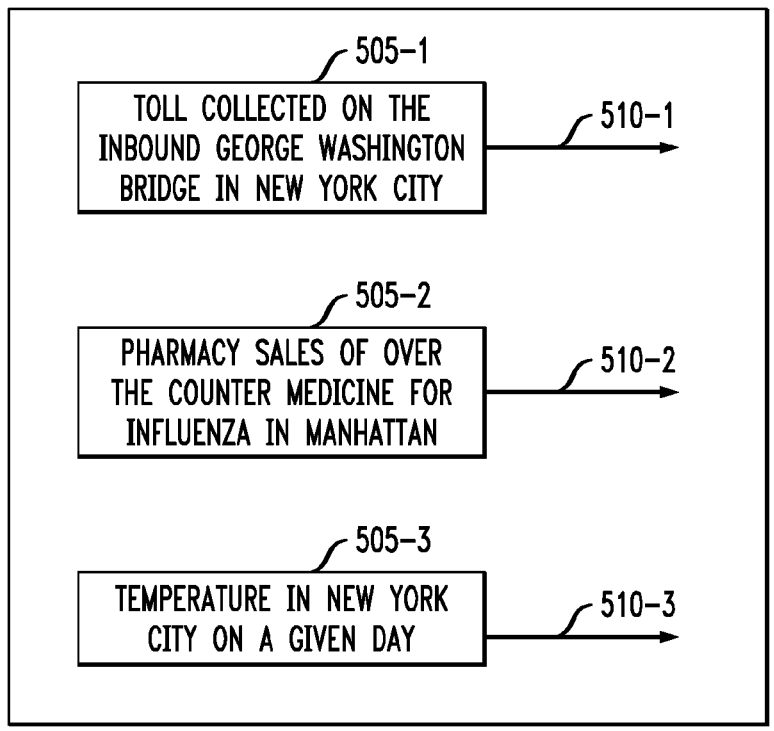
FIG. 5 is a block diagram illustrating three possible producers in an exemplary health monitoring scenario, in accordance with an exemplary embodiment of the present invention.

FIG. 5 shows three examples of producers in a health monitoring scenario. FIG. 5 shows exemplary heterogeneous information channels 510 created by producers 505. The producers 505 include tolls collected on the inbound George Washington bridge in New York City (producer 505-1, which produces information channel 510-1), weekly over-the-counter (OTC) drug sales for influenza in Manhattan (producer 505-2, which produces information channel 510-2), and daily temperature in New York City (producer 505-3, which produces information channel 505-3). Addition producers (not shown) could include relative humidity, precipitation, and such other variables, and these variables could be used to forecast the widespread outbreak of influenza. As another example, the OTC drug sales across all pharmacies in a city like New York can be aggregated and classified by the age-group of the buyers. Thus, information channels 510 can then be used to determine whether an outbreak of influenza is occurring, will occur, or has passed.

Figure 6:
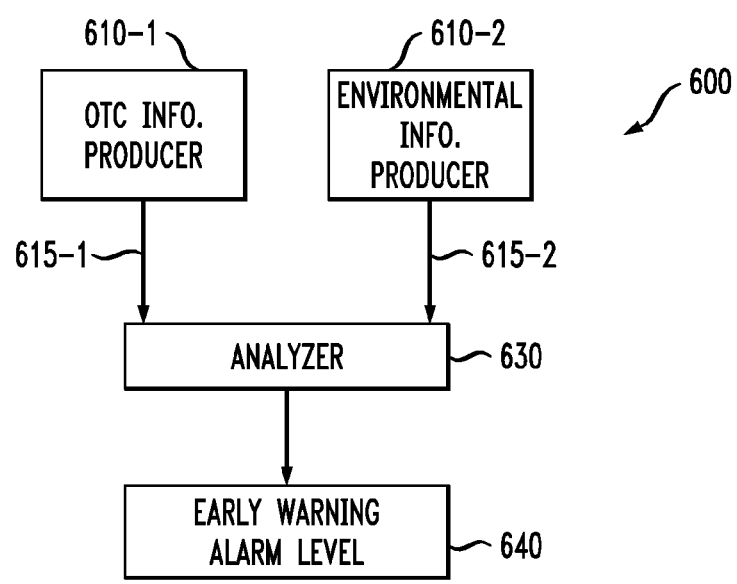
FIG. 6 is a block diagram illustrating, for an exemplary health monitoring scenario, a consumer that is an anomaly analyzer using two sets of information inputs from two different producers to produce an early warning alarm level for outbreak of a particular disease, in accordance with an exemplary embodiment of the present invention.

Illustratively, FIG. 6 shows an example of a consumer in a health monitoring scenario for a network portion 600, where the consumer is an anomaly analyzer 630. The anomaly analyzer 630 uses two sets of information channels 610 from two different producers 605, which are the OTC sales information producer 605-1 and the environmental information producer 605-2. The anomaly analyzer 630 uses two sets of information channels 610 to produce an early warning alarm level 640 for outbreak of a particular disease like influenza for the region over which the aggregated OTC sales and environmental information is made available. The early warning alarm level 640 is a metric that can be used to modify the value metric for a value network using the network portion 600. For example, the value metric could be the casualty figures due to such an outbreak.

It should be noted that FIG. 6 can also be considered to be a method. The analyzer 640 performs a step of analyzing information from the producers 610 in order to determine a metric 650.

Figure 7:
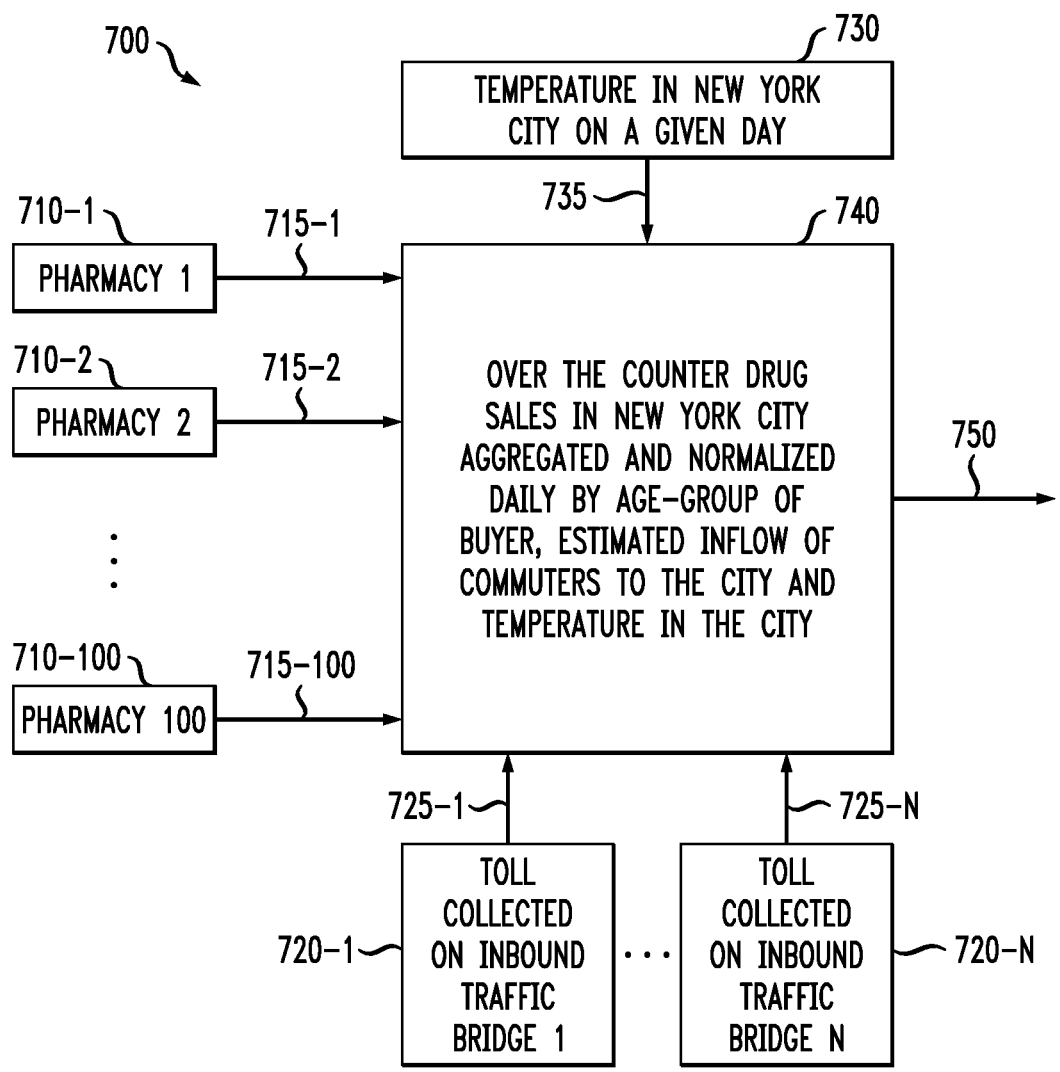
FIG. 7 is a block diagram illustrating a transducer, for an exemplary health monitoring scenario, that produces normalized aggregated age-based and population flow based drug sales information, in accordance with an exemplary embodiment of the present invention.

FIG. 7 shows an exemplary network portion 700 having a transducer 740 for a health monitoring scenario. Network portion 700 includes 100 pharmacy producers 710, each of which feeds OTC sales information over a corresponding one of the information channels 715 to the transducer 740, N toll bridge producers 720, each of which feeds toll collection information over a corresponding one of the information channels 725 to the transducer 740, a temperature producer 730 that feed daily temperature information over information channel 735 to transducer 740, and transducer 740. Transducer 740 produces, as output 750, normalized, aggregated age-based and population-flow-based drug sales information based on data incoming from multiple heterogeneous producers 710, 720, and 730. The transducer 740 converts information from one kind (e.g., sales, tolls, temperatures, etc.) into another kind such as aggregated normalized inputs, which can then be used by analyzers (e.g., consumers) looking for anomalies.

FIG. 7 may also be considered to be a method, where the transducer transduces and, in this example, normalizes information from the producers 710, 720, and 730.

Figure 8:
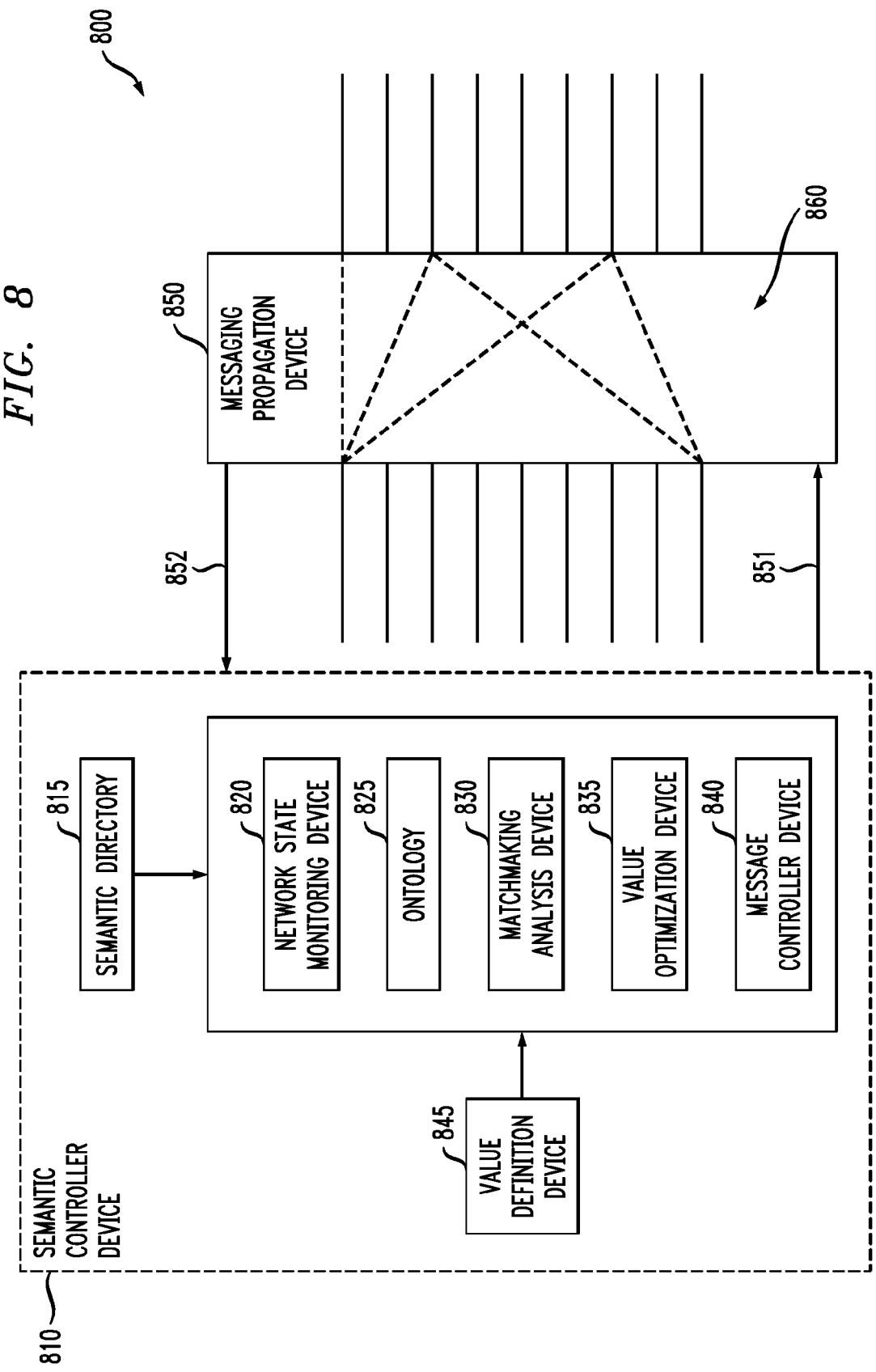
FIG. 8 is a block diagram of an exemplary semantic matchmaking device, in accordance with an exemplary embodiment of the present invention.

The dynamic and adaptive binding of various components of the value network can be achieved, in an exemplary embodiment, through the operation of a semantic matchmaking device 800 shown in FIG. 8. Semantic matchmaking device 800 is an exemplary representation of the semantic matchmaking device 135 shown in FIG. 1. In this example, the semantic matchmaking device 800 accepts from the system or the user a value metric, defined by the value definition device 845, that is to be modified. It should be noted that multiple value metrics can be used, if desired, but the value definition device 845 can also be adapted to define a single value metrics for multiple value metrics. For example, a value metric of "minimize time before an alert is issued for an influenza outbreak" and a value metric of "minimize casualties caused by an influenza outbreak" could be combined into a single value metric of "minimize time before an alert is issued for an influenza outbreak while minimizing casualties caused by an influenza outbreak."

Illustratively, the semantic matchmaking device 800 device can comprise two parts. One part is the messaging propagation device 850, and the other part is the semantic controller device 810. The semantic controller device 810 contains a semantic directory 815, a network state monitoring device 820, a number of ontologies (e.g., such as a federated ontology) of the network components, a matchmaking analysis device 830, a value optimization device 835, and a message controller device 840. The message controller device 840 is responsible for the activity on the messaging propagation device. The semantic controller device 810 uses a definition, provided by the value acceptance device 845, of the value metric to be optimized.

An exemplary operation of the semantic matchmaking device is explained through the following health monitoring scenario example.

Even a simple system using the consumers and producers described in FIGS. 5 and 6 can quickly become complicated to implement in the absence of exemplary embodiments of the present invention. First, there are several assumptions that can be used in a network enabling interoperability between participants:

1) If people are exposed to rainfall or snowfall and are not properly clad for the precipitation, they may catch a cold.

2) People buy OTC drugs when they think they are sick but do not think that the sickness severity warrants a visit to their doctor.

3) If an area is affected by flu, many people in that area will eventually buy OTC drugs for the common symptoms and this will be reflected in aggregated sales over a span of few days and within close geographical proximity.

Some of these assumptions that are made while designing a network enabling interoperability between participants may seem trivial but undoubtedly illustrate the kind of domain knowledge that can go into the design of components of the network. Similarly, the fact that OTC drug sales are designed to be transduced by transducers or produced by measurement devices also reflects domain knowledge. The output produced by the transducers or producers is interpreted based on knowledge. For example, the alarm level being high in winter is interpreted differently from the alarm level being high in summer or spring. Thus, there is a significant semantic component to the design, analysis and interpretation of transducers, producers and consumers. Current state of the art techniques do not however support any abstraction of this semantics. Thus, even if an abstraction of semantics is created, current techniques would not use the semantics. However, exemplary embodiments of the present invention can use the semantics when enabling interoperability between participants in a value network.

Examples are now listed of the tasks that one might expect to be used in a value network even in the case of the simplistic system of FIG. 1.

1) Some channels provide temperature in degrees Celsius while others provide them in degrees Fahrenheit. The feature extraction performed by exemplar embodiments of the present invention should be able to deal with the fact that temperature can be measured in different scales.

2) People buy some OTC drugs when there is a sale or when they know that a particular drug is not easily available and often is in short supply but is routinely needed. The feature extraction performed by exemplary embodiments of the present invention should thus be able to discount the effect of sales related to such drugs.

3) There is seasonality in many outbreaks such as the flu. Thus, high alarm levels during other seasons should quickly trigger alerts.

4) If a particular drug is replaced by a pharmaceutical company by another drug, the system should be able to determine this information and reconfigure itself.

Components of a value network should thus be able to abstract component requirements, assumptions and outputs so that efficient messaging propagation analysis and value optimization may be performed. For example, if it is raining and a work-site is being monitored, and assuming that the appropriate visual sensors are in place, the value network may want to know the number of people who walked in with an umbrella or wearing a raincoat. If this number is low and a pharmacy in the neighborhood, then communicates a sudden increase in the sale of OTC drugs for colds, the system should be able to relate the two events. Thus, the analyzer (e.g., a consumer) should be able to describe the semantics that the analyzer wants to analyze and not have to define the exact format and channel of the input information.

Enabling such and other types of interoperability is performed in an exemplary embodiment by the semantic matchmaking device 800. The semantic controller device 810, as part of the semantic matchmaking device 800, includes a semantic directory 815 that has semantics for components in a value network, such as the participants of consumers, producers, and transducers. Semantics for a consumer, for example, would define in the OTC medication example given above that certain sales are for medicines of a particular upper respiratory type of affliction. Thus, changes in brand names would not alter the count given by the producer of the medicines sold. Normalization could be performed by, for a given drug store, if the population within a certain area around the drug store is known, then the population could be used to determine the percentage of the population buying drugs for the upper respiratory type of affliction. The semantic directory 815 also defines interactions between the participants and defines the information produced or to be consumed by the participants. Interactions include data flow between participants. The message controller device 840 permits flow between participants and directs the flow, but at the same time the permission and direction of flow is based on the semantic definitions of inputs, outputs, and functionality of the participants (e.g., or other components) as defined in the semantic directory 815.

The semantic controller device 810 also includes one or more ontologies 825, such as a federated ontology, that help to provide appropriate and relevant inputs to components and to interpret the produced outputs of the components.

The semantic controller device 810 additionally includes a value optimization device 830 that optimizes the value metric of the network in conjunction with the network state device and the other components of the semantic matchmaking device. The value definition device 845 defines the value metric. Finally, the semantic matchmaking device 800 contains the messaging propagation device 850 that controls the flow of information in the messaging propagation device 850. It is through the messaging controller device 850 that the semantic controller device 810 effects and directs efficient adaptive flow of information in the value network to achieve an optimal value of the value metric or to modify a value of the value metric. The semantic controller device 810 uses one or more control signals 851 and one or more feedback signals 852 when controlling the messaging propagation device 850. The linkages 860 are directed by the semantic controller device 810 and the semantic controller device 810 makes these linkages 860 dynamic. In an exemplary embodiment, the semantic matchmaking device 800 directs and provides connectivity based generally on a high-level semantic analysis of the components of the value network and the optimization criteria driving the interconnection is the value metric used to determine value for the network.

The matchmaking analysis device 830 drives information flow between producers, consumers, and transducers that are semantically related. The matchmaking analysis device 830 will link participants the matchmaking analysis device 830 determines will lead to the modification of the value metric defined by the value definition device 845. It should be noted that the matchmaking analysis device 830 could link two participants (for instance), then determine over some period of time that the linkage in information flow between the two participants worsens the value metric and therefore the matchmaking analysis device 830 could unlink the two participants.

Figure 9:
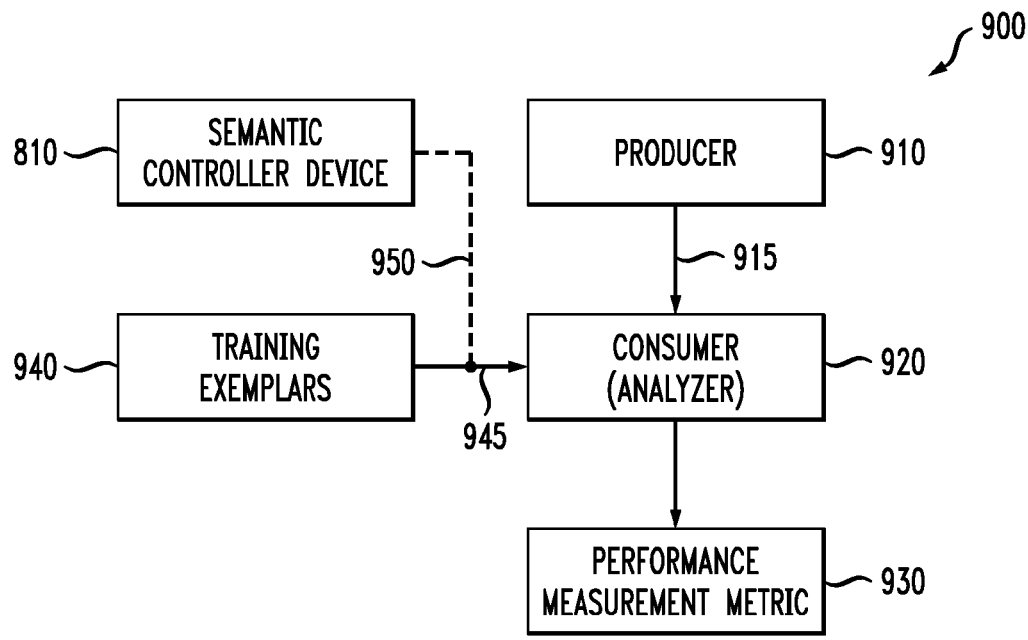
FIG. 9 is a block diagram illustrating adaptation of a consumer to optimize the contribution of the consumer to a total value of a network, in accordance with an exemplary embodiment of the present invention.

In addition to adaptive and directed information flow, the semantic matchmaking device 800 also can control the adaptation of components of the network. For example, based on newly supplied information, the semantic matchmaking device 800 can send a request to a network component to adapt itself as shown in FIG. 9. FIG. 9 shows the adaptation of a consumer based on supervision through manually labeled exemplars. FIG. 9 shows an exemplary network portion 900 comprising the semantic controller device 810, a producer 910 that produces information on information channel 915, a consumer 920 that is coupled to the information channel 915 and that produces a performance measurement metric 930, and training exemplars 940. The semantic controller device 810 causes the training exemplars to be directed to the consumer 920 by using the information channel 945 (as set up by the messaging propagation device 850, for instance, which is not shown in FIG. 9). The training exemplars 920 then cause behavior of the consumer 920 to change. For instance, the training exemplars 940 could show that the number of OTC drugs purchased in a two week time period is lower than originally determined, and the consumer 920 will modify calculations used to determine the performance measurement metric 930 in light of the training exemplars.

Another technique for changing the behavior of the consumer 920 is by having the semantic controller device 810 perform a statistical analysis of the current behavior of the consumer 920 with respect to participants within a predetermined distance from the consumer 920 and that are reachable by information channels from the consumer 920. For instance, if other participants experience errors and the errors can be statistically determined to be caused by the consumer 920, then the semantic controller device 810 can modify the behavior of the consumer 920 by providing additional information (in the form of training exemplars 940 or other information) to the consumer 920 to change the behavior of the consumer 920. The statistical analysis could be determined by determining how many participants have errors, how much data is being transferred from or to the consumer 920, and how often the consumer 920 provides data over information channels. Any statistics associated with the component (e.g., consumer 920) can be used.

Figure 10:
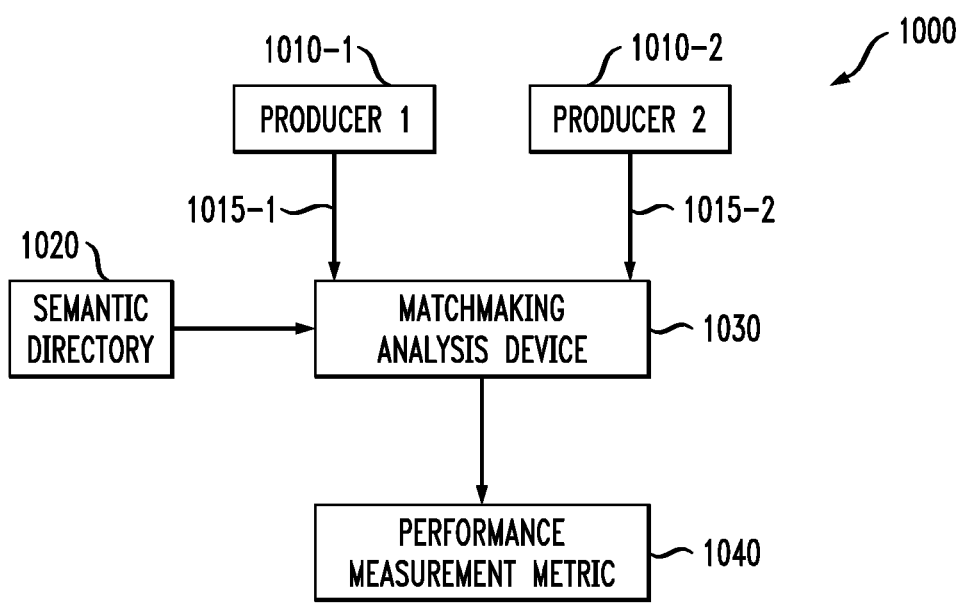
FIG. 10 is an exemplary block diagram illustrating a matchmaking analyzer discovering a relationship between multiple participants through analysis of a semantic directory corresponding to the participants and based on the performance of the participants, as measured by performance metrics, in accordance with an exemplary embodiment of the present invention.

Of the adaptations that can result in dynamic alignment of various components of the network, the most typical changes arise due to temporary or permanent emergence or disappearance of producers and consumers. A network portion 1000 is shown in FIG. 10 and the network portion includes two producers 1010 producing two information channels 1015 that are coupled to a matchmaking analysis device 1030, the matchmaking analysis device 1030, a semantic directory 1020, and a performance measurement metric 1040. The semantic directory 1020 is an example of the semantic directory 815 of FIG. 8, and the matchmaking analysis device 1030 is an example of a matchmaking analysis device 830 of FIG. 8.

FIG. 10 also shows an exemplary method by which the matchmaking analysis device 830 in a semantic controller device (e.g., semantic controller device 810) can automatically model relationships between different components so that the semantic controller device can be used to align one or more of the components. For example, the matchmaking analysis device 1030 can automatically learn, through techniques known to those skilled in the art, that producers 1010-1 and 1010-2 are highly correlated and that one producer can be replaced by another in the absence of one of them.

The performance measurement metric 1040 is used when modifying the value metric of the value network. However, the relationship between the performance measurement metric 1040 and the value metric may not be a simple relationship. As an illustration, the value metric might be maximizing revenues or minimizing casualties. The value metric in turn can be converted into numerous low level metrics, like "meet targeted number of consumers," "do not exceed targeted levels of inventory," or "have a precision of over 90 percent in detecting a terror attack." The low level metrics, such as performance measurement metric 1040 can be used by the value optimization device 835 (see FIG. 8) when the semantic controller device 810 performs operations to modify the value metric.

Illustratively, the matchmaking analysis device 1030 uses semantic models in the semantic directory 1020 and the performance measurement metric 1040 when learning whether the producers 1010-1 and 1010-2 are correlated. For instance, if the performance measurement metric 1040 is benefited by using solely producer 1010-1 or by using solely producer 1010-2 and the benefit incurred is about equal for each producer 1010, then the matchmaking analysis device 1030 could substitute one producer 1010 for another (e.g., producer 1010-2 could be used instead of producer 1010-1). However, the matchmaking analysis device 1030 may also determine that using information channels 1015 from both producers together create a benefit for the performance measurement metric 1040. For instance, if it is winter as determined by producer 1010-1 and it is cold as determined by producer 1010-2, the metric of "possibility of a flu outbreak" might be higher if it is both winter and cold, than if it is winter but not cold or if it is cold but not winter.

Figure 11:
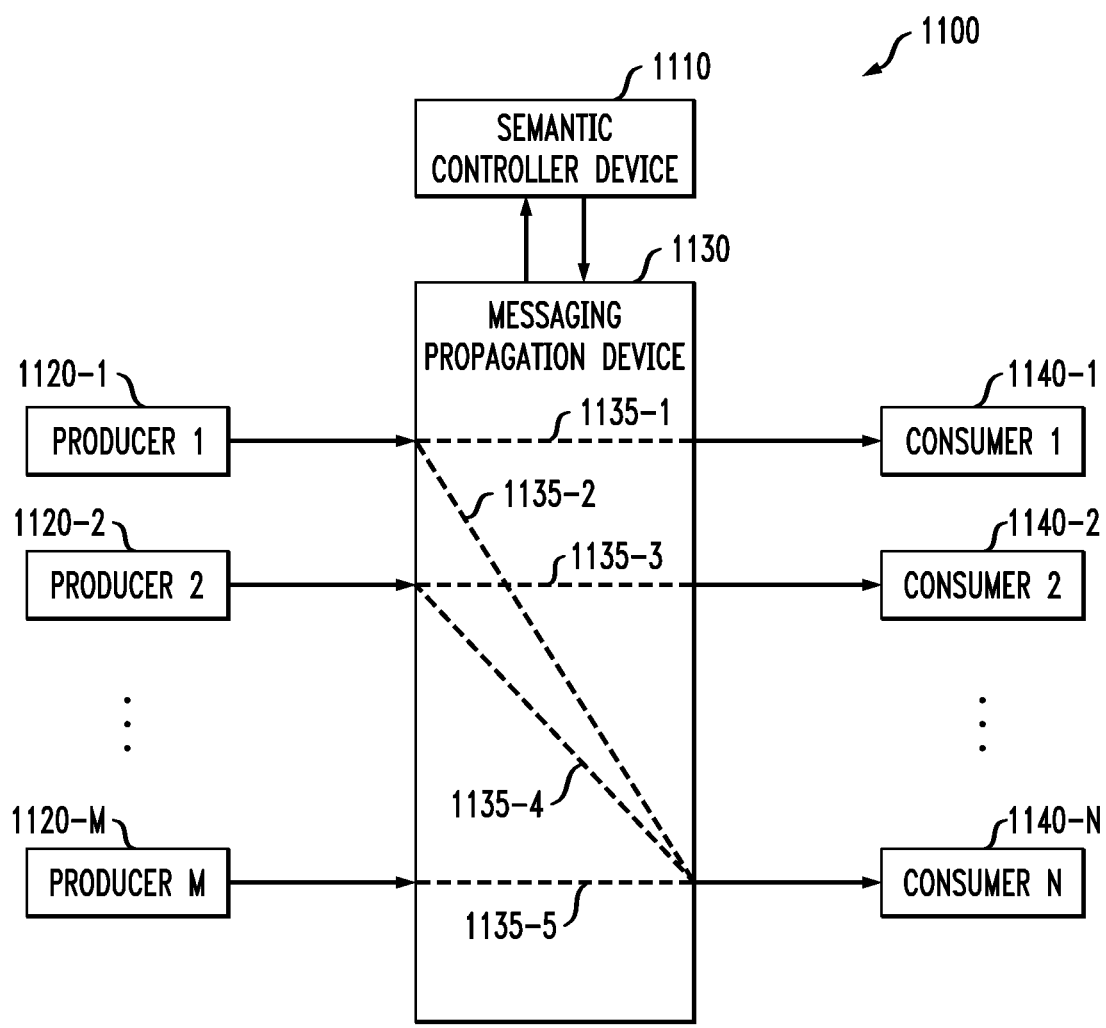
FIG. 11 is an exemplary block diagram of a snapshot of adaptive matchmaking of producers and consumers at a particular state in time, where dashed connections represent dynamic linkages between producers and consumers, in accordance with an exemplary embodiment of the present invention.
Figure 12:
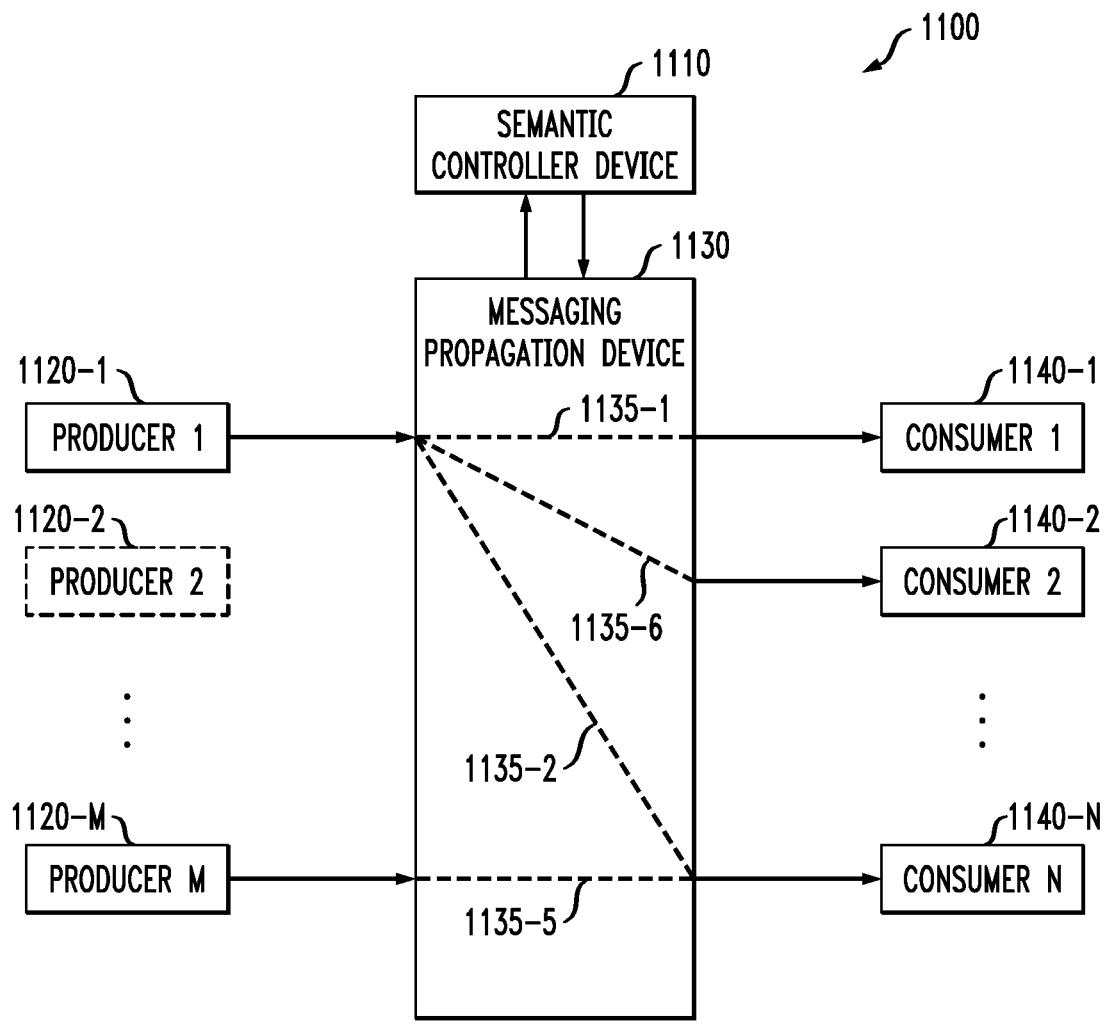
FIG. 12 is a block diagram of the adaptive matchmaking of FIG. 11 at a different state in time, when producer 2 has been deleted from the network, in accordance with an exemplary embodiment of the present invention.

FIGS. 11, 12, and 13 illustrate adaptive control of information flow in order to enable interoperability between participants in a network.

FIG. 11 shows a snapshot of the adaptive matchmaking of producers 1120-1 through 1120-M and consumers 1140-1 through 1140-N at a particular state in time. In network portion 1100, the semantic controller device 1110 has directed the messaging propagation device 1130 to set up information flow as shown in FIG. 11. Linkages 1135 are dynamic and are between producers 1120 and consumers 1140 at the current state. In this state, the consumer 1140-N is linked with producers 1120-1, 1120-2 and 1120-M. Meanwhile, consumer 1140-1 is linked to producer 1120-1 and consumer 1140-2 is linked to producer 1120-2.

Now assume that producer 1120-2 drops out such as by being unresponsive or sending a "removal" message. FIG. 12 shows another snapshot of the network portion 1100 at a different state in time. Dashed connections represent the dynamic linkage between producers and consumers within the state. Notice that the producer 1120-2 is missing (as shown by a dashed line on producer 1120-2) in this state and hence the linkages 1135-3 and 1135-4 are deleted. Instead, consumer 1140-2 is now linked to producer 1120-1 through linkage 1135-6. This can for example be based on analysis as shown in and described in reference to FIG. 10 that results in the identification that producer 1120-1 is the most highly correlated producer 1120 to producer 1120-2 and hence can be used in place of producer 1120-2. Linkages 1135 are created, maintained, deleted, and replaced based on semantic models for the producers 1120 and the consumers 1140, where the semantic models are typically listed in a semantic directory (not shown in FIG. 12). Note that the semantic controller device 1110 could determine that a producer or other participant should be deleted from the network and therefore can be removed from the network. For instance, a producer could be redundant (for instance, produces results that are fungible with other results) or a transducer could produce erroneous or invalid results.

FIG. 13 offers another snapshot of the same network portion 1100 at a different state in time. Notice that a new producer 1320 is now available. Sometime after the new producer 1320 becomes available and lists itself in the semantic directory (not shown in FIG. 13), the semantic model for the new producer 1320 is analyzed by the semantic controller device 1110 and the information (typically an information channel) from the new producer 1320 is appropriately linked to consumer 1140-2 through linkage 1135-7.

The determination to link the new producer 1320 to the consumer 1140-2 can be based, for example, on the information that the new producer 1320 lists in the semantic directory. For instance, producer 1120-2 may have produced information of the number of fever reduction capsules for children sold over the counter in New York City. The new producer 1320 that is now used to replace the producer 1120-2 may be the number of elementary school absentees in New York City reportedly absent due to flu. Since both producers 1320, 1120-2 have listed (e.g., through a semantic model) their abstract information type in the semantic directory, it is possible for the matchmaking analysis device of the semantic controller device 1110 to determine that information from the new producer 1320 can be used by the consumer 1140-2, and the semantic controller device 1110 will direct the messaging propagation device 1130 to create linkage 1135-7 in order to route the information from the new producer 1320 to the consumer 1140-2.

Turning now to FIG. 14, a computer system 1400 is shown that is suitable for implementing one or more components of a value network, such as a semantic matchmaking device. Computer system 1400 includes a processor 1410 that is singular or distributed, a memory 1420 that is singular or distributed, a network interface 1430, and a media interface 1440. The network interface 1430 couples to a network 1470 (e.g., portions of a value network). The media interface 1440 couples to a computer readable medium 1460, which includes one or more programs (not shown) which, when implemented, carry out portions or all of the present invention. For example, the semantic matchmaking device 800 can be included as a program. The program, when loaded into processor 1410 (typically from memory 1420), will configure the processor 1410 to implement the semantic matchmaking device 800.

It is to be understood that the embodiments and variations shown and described herein are merely illustrative of the principles of this invention and that various modifications may be implemented by those skilled in the art without departing from the scope and spirit of the invention.

What is claimed is:

1. A method for enabling interoperability between a plurality of participants in a network, the method comprising the steps of:
   determining a value associated with a value metric defined for at least a portion of the network;
   determining two or more alternative information flows between two or more of the plurality of participants in the network based at least in part on one or more semantic models corresponding to the plurality of participants and on the value associated with the value metric, wherein the one or more semantic models define inputs, outputs, and functionality for each of the plurality of participants and define at least a portion of information produced or consumed by the plurality of participants; and
   optimizing an overall value of the network by selecting combinations of said alternative information flows for at least one portion of the network in order to satisfy consumers of information, wherein one or more steps are performed by a processor.

2. The method of claim 1, wherein the step of determining two or more alternative information flows further comprises the steps of:
   performing matchmaking between the plurality of participants based on the one or more semantic models and the value; and
   directing information flow between the participants matched during the matchmaking.

3. The method of claim 2, wherein the step of matchmaking comprises the steps of:
   determining by using the one or more semantic models that the participants can be connected; and
   determining that the value metric is modified by the connection.

4. The method of claim 1, further comprising the step of normalizing the portion of information based on the one or more semantic models, and wherein the step of determining two or more alternative information flows uses the normalized portion of information.

5. The method of claim 1, further comprising the step of performing the determining steps multiple times in order to modify the value associated with the value metric.

6. The method of claim 1, wherein the steps of determining are completed a number of times in order to modify the value associated with the value metric from one or more initial values to one or more final values, wherein each of the number of times the steps of determining are completed creates one or more intermediate values associated with the value metric, and wherein the one or more final values are selected when changes in directing information between two or more of the plurality of participants cause currently determined one or more intermediate values to be within a predetermined distance from previously determined one or more intermediate values.

7. The method of claim 1, further comprising the step of generating one or more alerts based on the value of the value metric.

8. The method of claim 1, wherein the step of determining two or more alternative information flows further comprises the steps of:
   inserting a new participant into the network based on a semantic model of the new participant; and
   directing information flow between one or more existing participants and the new participant.

9. The method of claim 1, wherein a given participant has information flow coupled to one or more particular participants, and wherein the step of determining two or more alternative information flows further comprises the steps of:
   determining that the given participant has been removed from the network; and
   directing information, by using the one or more semantic models, from one or more existing participants to the one or more particular participants.

10. The method of claim 9, wherein the step of determining two or more alternative information flows further comprises the steps of determining that the given participant can be deleted from the network and deleting the given participant from the network.

11. The method of claim 1, wherein the step of determining two or more alternative information flows comprises the step of directing new information to a given participant, whereby behavior of the given participant can change in response to the new information.

12. The method of claim 11, wherein the step of determining two or more alternative information flows further comprises the step of performing an analysis of statistical behavior of the given participant with respect to participants within a predetermined distance in the network from the given participant.

13. The method of claim 1, wherein the step of determining two or more alternative information flows uses a semantic directory to access the one or more semantic models.

14. The method of claim 13, wherein the semantic directory lists one or more of services, assumptions and processing methodologies of the plurality of participants.

15. The method of claim 14, further comprising the step of externalizing the services, assumptions, and processing methodologies of the plurality of participants, wherein the externalization is performed using one or more of specifically designed ontologies and federated ontologies.

16. The method of claim 1, wherein the participants of the network comprise producers of information, consumers of information, and transducers of information.

17. The method of claim 16, wherein the transducers convert information from one kind to another kind.

18. The method of claim 1, wherein one or more of the participants produce a low level metric, and wherein the step of determining a value uses the low level metric.

19. The method of claim 1, wherein the value metric comprises one or more of a rule, an equation that evaluates to a value, and a boolean rule.

20. An apparatus for enabling interoperability between a plurality of participants in a network, the apparatus comprising:
- one or more memories; and
- one or more processors coupled to the one or more memories, the one or more processors configured:
  - to determine a value associated with a value metric defined for at least a portion of the network;
  - to determine two or more alternative information flows between two or more of the plurality of participants in the network based at least in part on one or more semantic models corresponding to the plurality of participants and on the value associated with the value metric, wherein the one or more semantic models define inputs, outputs, and functionality for each of the plurality of participants and define at least a portion of information produced or consumed by the plurality of participants; and
  - to optimize an overall value of the network by selecting combinations of said alternative information flows for at least one portion of the network in order to satisfy consumers of information.

21. The apparatus of claim 20, wherein the one or more processors are further configured, when directing information flow:
- to perform matchmaking between the plurality of participants based on the one or more semantic models and the one or more values; and
- to directing information flow-between the participants matched during the matchmaking.

22. The apparatus of claim 20, wherein the one or more processors are further configured to perform the determining steps multiple times in order to modify the value associated with the value metric.

23. The apparatus of claim 20, wherein the determining operations are completed a number of times in order to modify the value associated with the value metric from one or more initial values to one or more final values, wherein each of the number of times the determining operations are completed creates one or more intermediate values associated with the value metric, and wherein the one or more final values are selected when changes in directing information between two or more of the plurality of participants cause currently determined one or more intermediate values to be within a predetermined distance from previously determined one or more intermediate values.

24. The apparatus of claim 20, wherein the one or more processors are further configured to generate one or more alerts based on the value of the value metric.

25. The apparatus of claim 20, wherein the one or more processors are further configured, when directing information flow:
- to insert a new participant into the network based on a semantic model of the new participant; and
- to direct information flow between one or more existing participants and the new participant.

26. The apparatus of claim 20, wherein a given participant has information flow coupled to one or more particular participants, and wherein the one or more processors are further configured, when directing information flow:
- to determine that the given participant has been removed from the network; and
- to direct information, by using the one or more semantic models, from one or more existing participants to the one or more particular participants.

27. The apparatus of claim 20, wherein the one or more processors are further configured, when directing information flow, to direct new information to a given participant, whereby behavior of the given participant can change in response to the new information.

28. The apparatus of claim 20, wherein the one or more processors are further configured, when directing information flow, to use a semantic directory to access the one or more semantic models.

29. The apparatus of claim 20, wherein the participants of the network comprise producers of information, consumers of information, and transducers of information.

30. The apparatus of claim 20, wherein one or more of the participants produce a low level metric, and wherein the one or more processors are further configured, when determining the value, to use the low level metric when determining the value.

31. The apparatus of claim 20, wherein the value metric comprises one or more of a rule, an equation that evaluates to a value, and a boolean rule.

32. An article of manufacture for enabling interoperability between a plurality of participants in a network, the article of manufacture comprising:
- a non-transitory computer readable recordable medium containing one or more programs which when executed implement the steps of:
- determining a value associated with a value metric defined for at least a portion of the network;
- determining two or more alternative information flows between two or more of the plurality of participants in the network based at least in part on one or more semantic models corresponding to the plurality of participants and on the value associated with the value metric, wherein the one or more semantic models define inputs, outputs, and functionality for each of the plurality of participants and define at least a portion of information produced or consumed by the plurality of participants; and
- optimizing an overall value of the network by selecting combinations of said alternative information flows for at least one portion of the network in order to satisfy consumers of information.

* * * * *